(12) United States Patent
Tanaka et al.

(10) Patent No.: US 7,060,046 B2
(45) Date of Patent: Jun. 13, 2006

(54) PELVIS CORRECTION APPARATUS

(76) Inventors: Masaru Tanaka, 2-33-6, Narimasu, Itabashi-ku, Tokyo 175-0094 (JP); Masato Tanaka, 2-33-6, Narimasu, Itabashi-ku, Tokyo 175-0094 (JP)

( * ) Notice: Subject to any disclaimer, the term of this patent is extended or adjusted under 35 U.S.C. 154(b) by 278 days.

(21) Appl. No.: 10/697,025

(22) Filed: Oct. 31, 2003

(65) Prior Publication Data

US 2005/0096700 A1    May 5, 2005

(51) Int. Cl.
*A61F 5/00* (2006.01)

(52) U.S. Cl. ................ 602/33; 602/32; 5/621

(58) Field of Classification Search .............. 602/33, 602/35, 36, 32; 5/621, 624, 648, 650
See application file for complete search history.

(56) References Cited

U.S. PATENT DOCUMENTS 4,073,290 A * 2/1978 Farrar, Jr. .............. 602/36

* cited by examiner

*Primary Examiner*—Henry Bennett
*Assistant Examiner*—Camtu Nguyen
(74) *Attorney, Agent, or Firm*—Birch Stewart Kolasch & Birch LLP

(57) ABSTRACT

A pelvis correction apparatus is disclosed, by which appropriate pelvis correction therapy is performed with application of sufficient pressing force at a predetermined angle to a patient by simple operation irrespective of therapist's skill. The apparatus includes a bed, pressing bars which moves from both sides of the bed toward a pelvis of the patient on the bed with a predetermined inclination angle, the pressing bars having pressing members on one ends, the pressing members brought into contact with the patient to convey pressing force to the pelvis, and a member for urging the movement of the pressing bars.

10 Claims, 6 Drawing Sheets

PELVIS CORRECTION APPARATUS

BACKGROUND OF THE INVENTION

1. Field of the Invention

The present invention relates to pelvis correction apparatus for preventing or curing various symptoms accompanied by pain due to variation of the state of a pelvis.

2. Description of the Related Art

All of the weight of his upper half body is applied to the pelvis area of humans. As a result, a severe load may be applied to the joints (sacro-iliac joint) between the sacrum at the lower end of the vertebral column and the pelvis, constituting the hip. FIG. 8 schematically shows a structure of a sacrum and a pelvis. A joint 300 between the sacrum 100 and the pelvis 200 is formed by the combination of surfaces called "auricular surfaces". That is, the auricular surfaces of the sacrum 100 and the auricular surfaces of iliac bones 200b occupying the upper rear portion of coxal bones 200a constituting the pelvis 200 together constitute the joint between the sacrum 100 and the pelvis 200.

When excessive loads are applied to the pelvis from various undesirable directions, the auricular surfaces are forced to vary the state in which they are situated and various symptoms accompanied by pain may sometimes be developed. An excessive load may be applied, for example, when a person twists his waist or lifts a heavy load while twisting and/or bending the body and application of such an excessive load may cause the auricular surfaces to be displaced from the normal positions and result in a distorted pelvis.

In addition, application of an excessive load to the pelvis due to overweight and weakened ligament due to insufficient exercise may also cause the above-mentioned problem.

In view of the above, pelvis correction has conventionally been applied by embracing the sacrum and iliac bone from a substantially vertical direction by a therapist using his/her fingers or arms to thereby eliminate laxity or disengagement of auricular surfaces or the like to ensure connection between the sacrum and the iliac bone.

However, in this conventional pelvis correction, because the pelvis is pressed using a force applied by a therapist's fingers or arms, it is difficult, even for an experienced therapist, to stably apply a sufficient pressing force at a constant angle. Moreover, it is also difficult to practice this conventional pelvis correction with a patient having hard muscles, like an athlete, or a large person, because these people have well-developed ligament.

OBJECT AND SUMMARY OF THE INVENTION

The present invention has been conceived in view of the above and it is therefore an object of the present invention to provide a pelvis correction apparatus which can stably apply a sufficient pressing force at a constant angle, for a simple operation and regardless of the skill of a therapist, so that appropriate treatment can be attained and hip pain can be prevented.

The above-mentioned object is achieved by a pelvis correction apparatus, comprising a bed for a patient to receive a treatment; pressing bars provided so as to move at a constant inclination angle from both sides of the bed toward a pelvis of the patient to receive a treatment while lying on the bed and each of the pressing bars having a pressing member attached to a tip end of the pressing bar to abut on the patient to transmit a pressing force to the pelvis of the patient; and an urging member which urges the pressing bars to move toward the pelvis of the patient while lying on the bed.

With this arrangement, a pressing force can be applied to the pelvis of a patient lying on the bed to receive a treatment, using a stable force generated by the pressing bars urged to move from the respective sides of the bed toward the pelvis of the patient. As the pressing force depends on an urging force of the urging member, it is possible, by adjusting the urging member, to apply a pressing operation by the pressing bars using a pressing force which is suitable for each patient.

It should be noted that the urging means is not limited to a stretchable member such as rubber, and an air or hydraulic cylinder having a pressure adjustable valve may be used.

The above object is also achieved by a pelvis correction apparatus wherein a structure for mounting the pressing bars has a pressing bar bearing stand which is situated on each of right and left sides of the bed and has a vertically extending horizontal slit formed on the pressing bar bearing stand, and a pressing bar holder which has a tube member allowing the pressing bar to slide inside of the tube member and is fixed such that a vertical position of the pressing bar holder in the slit is adjustable.

According to the above described structure, a structure in which pressing bars moves at a predetermined inclination angle from both sides of the bed towards the pelvis of a patient lying on the bed to receive treatment can be realized using a simple structure.

In particular, because the vertical position of the pressing bar holder is readily adjustable by sliding the holder along the slit and, moreover, the pressing bar slides inside the tube member provided to the pressing bar holder, stable pressing onto the pelvis at a precise angle can be always attained.

The above object is also achieved by a pelvis correction apparatus wherein the urging member which urges the pressing bar to move toward the pelvis of the patient comprises a stretchable member provided to connect the pressing bars to urge the pressing bars to move toward each other.

According to this structure, the pressing bar can be urged to move toward the pelvis of a patient using a simple structure. A rubber belt or spring may be used as a stretchable member and the strength of the urging force can preferably be selected as desired.

The above object is also achieved by a pelvis correction apparatus according, wherein the pressing bars are provided two on each of the right and left sides of the bed so as to press the pelvis of the patient at two points respectively on right and left sides of the pelvis.

The above object is also achieved by a pelvis correction apparatus, wherein the two pressing bars provided on each side of the bed are mounted such that one pressing bar is mounted at an upper position and the other pressing bar is mounted to a lower position, a first pair of pressing bars mounted at the upper positions are held such that pressing members attached to respective tip ends of the pressing bars incline downward at a predetermined angle and move toward the pelvis while keeping the inclination angle, and a second pair of pressing bars mounted at the lower positions are held such that pressing members attached to respective tip end of the pressing bars incline upward at a predetermined angle and move toward the pelvis while keeping the inclination angle.

During the treatment, a patient remains lying on the bed with his/her face up or down. In order to treat the patient lying as described by pressing from his/her right and left sides, it is preferably to simultaneously apply a pressing force from points at different heights. Therefore, two pressing bars are mounted at different heights on each side of the bed so that a pressing force is applied from points at different heights on the right and left sides of the bed. With this arrangement, well-balanced precise correction is achieved.

The above object is also achieved by the pressing member attached to the tip end of each pressing bar is provided to be swingable around an axial center of the pressing bar.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

In the following, embodiments of the present invention will be described in detail with reference to the accompanied drawings.

Figure 1:
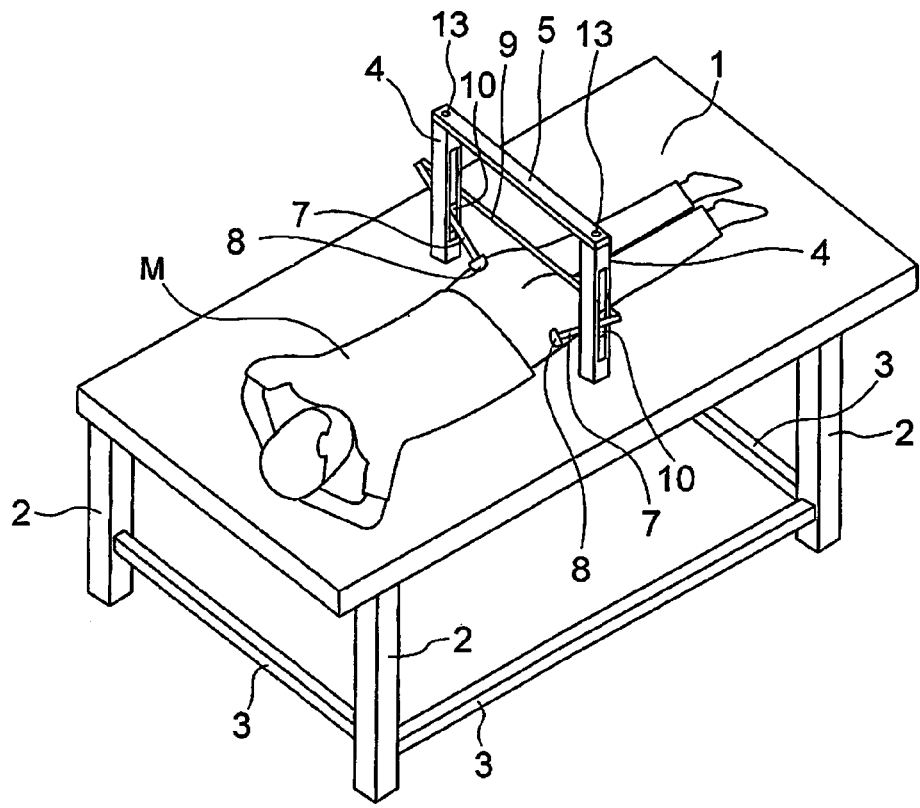
FIG. 1 is a perspective view showing a pelvis correction apparatus in an embodiment of the present invention.
Figure 2:
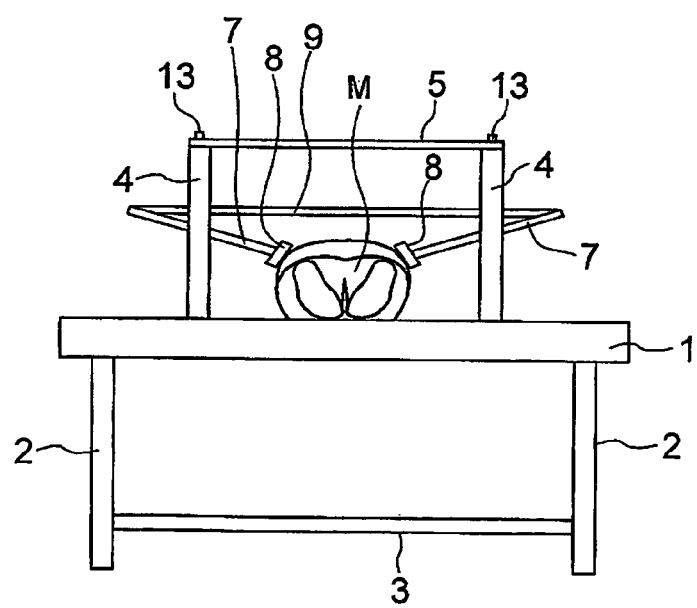
FIG. 2 is an end view of the pelvis correction apparatus of FIG. 1.

FIGS. 1 and 2 are diagrams showing an example of a pelvis correction apparatus having the simplest structure according to the present invention. FIG. 1 is a perspective view showing a pelvis correction apparatus in an actual use and FIG. 2 is an end view of the pelvis correction apparatus of FIG. 1.

As shown in FIGS. 1 and 2, the pelvis correction apparatus comprises a rectangular bed 1 where a patient M lies. The bed 1 is supported by four supporting legs 2 and a reinforcement member 3 is provided between the adjacent supporting legs 2. Note that the supporting legs are not indispensable, and a bed 1 having no supporting legs may also be usable.

On the bed 1, two pressing bar bearing stands 4 are respectively provided on the right and left sides relative to the centerline of the bed 1. Specifically, the pressing bar bearing stands 4 stand at respective positions near the right and left opposing sides of the bed 1 such that a patient M can lie between the stands 4 with some space between the stands 4 and the patient. An upper reinforcement member 5 is provided to horizontally bridge the pressing bar bearing stands 4 so as to prevent the stands 4 from declining during use of the apparatus. Both ends of the upper reinforcing member are fixed to the respective top ends of the pair of pressing bar bearing stands 4 using bolts 13.

Each pressing bar bearing stand 4 has a hollow structure and a pressing bar 7 is mounted to the pressing bar bearing stand 4 such that the vertical position of the pressing bar 7 is freely adjustable. The pressing bar 7 is mounted such that the one end is directed to the pelvis of a patient M lying on the bed 1.

Mounting of the pressing bar 7 is achieved using a pressing bar holder. The pressing bar holder comprises a block body 10 and a tube member 20 which is attached to the block body 10 so as to extend therethrough. The tube member 20 provides a path along which the pressing bar 7 moves. That is, the tube member 20 is constructed such that the pressing bar 7 can slide inside of the tube member 20.

Figure 3:
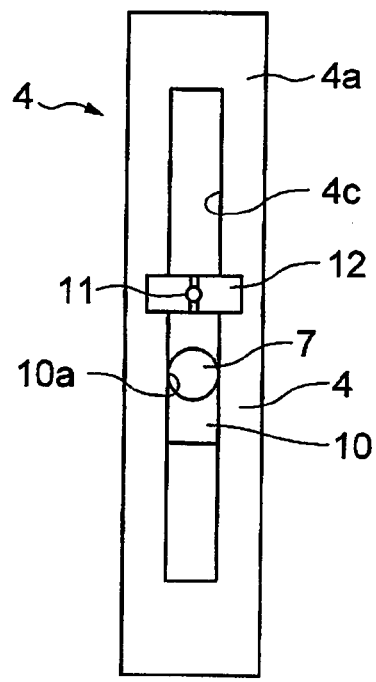
FIG. 3 is a front side view of a stand shown in FIG. 1.
Figure 4:
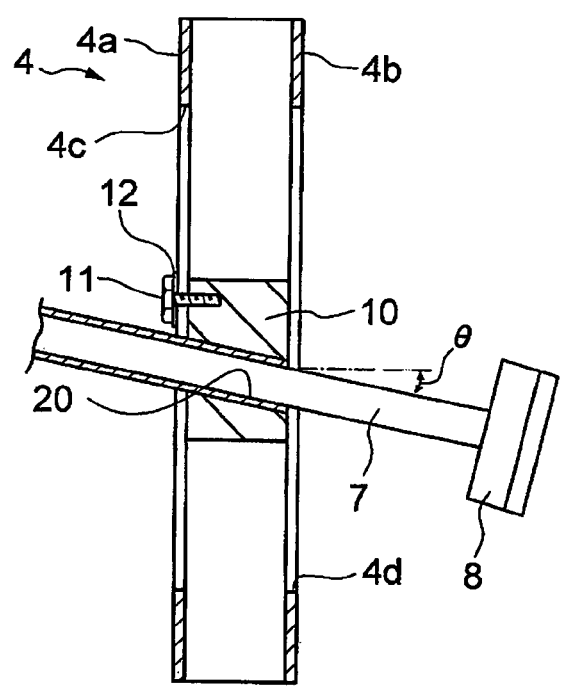
FIG. 4 is a cross sectional view in the longitudinal direction of the stand shown in FIG. 1.

FIGS. 3 and 4 show an exemplary manner of mounting the pressing bar 7 to the pressing bar bearing stand 4. The pressing bar bearing stand 4 has a substantially rectangular external shape and a hollow structure as shown so that the block body 10 can vertically move inside the stand 4. The pressing bar bearing stand 4 has also two vertically extending slits 4c, 4d formed on the respective opposing flank walls 4a and 4b of the stand 4. The block body 10 may be made from aluminum or the like.

The block body 10 is fixed to the pressing bar bearing stand 4 using a plate 12 and a screw 11. That is, a plate 12 is placed on the outer surface of the flank wall 4a of the pressing bar bearing stand 4 where the slit 4c is formed, so as to extend across the slit 4c in the width direction, and a screw 11 is then threaded into the plate 12 and the block body 10 through the slit 4c whereby the plate 12 is fixed to the block 10 and thus to the pressing bar bearing stand 4.

Since the pressing bar 7 is incorporated into the tube member 20 which extends through the block body 10, the vertical position of the pressing bar 7 can be adjusted by adjusting the vertical position of the block body 10 in the slit. Moreover, since the pressing bar 7 extends through the slits 4c and 4d together with the tube member 20, the angle of inclination (angle θ) is set according to the inclination of the tube member 20. This inclination angle is an angle appropriate to achieve precise pressing onto the pelvis of a patient M.

The inner diameter of the tube member 20 is set appropriate relative to the outer diameter of the pressing bar 7, such that a stable axial movement of the pressing bar 7 without shake, that is, a sliding movement of the pressing bar inside the tube member 20, is ensured.

As shown in FIG. 4, a pressing member 8 is attached to one end of the pressing bar 7 for direct contact with the patient M to transmit a pressing force from the pressing bar 7 to the patient M. The surface of the pressing member 8 which contacts the patient M is formed as substantially flat so as to modify the sense of being pressed which the patient M may feel when pressed at his hip.

As is appreciated from FIGS. 1 and 2, a rubber belt 9 is provided as an urging member to connect the respective other ends of the pair of pressing bars 7. Installation of the rubber belt 9 is achieved by attaching the end of the rubber belt 9 to a hook (not shown) attached to the other end of the pressing bar 7.

With this arrangement, the pressing bars 7 are always forced toward each other. That is, when a patient M lies on the bed 1, the respective pressing bars 7 press the pelvis of the patient M by means of a contracting force of the rubber belt 9. The length of each pressing bar 7 is determined so as to achieve reliable pressing onto the patient M regardless of the patient M's size. It should be noted that the urging member is not limited to a rubber belt 9 but may be any other member which can appropriately apply an urging force to the pressing bar 7. For example, a spring may be applicable.

Figure 5:
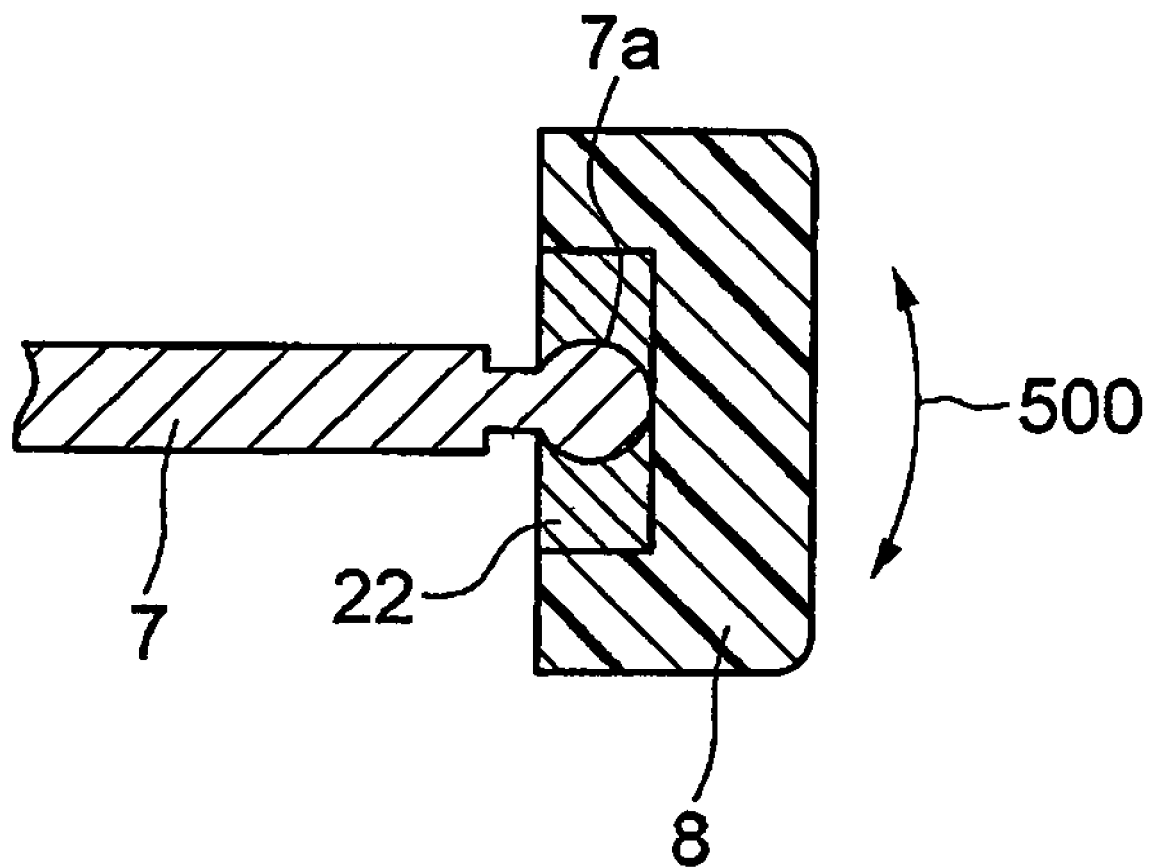
FIG. 5 is a cross sectional view of a pressing bar and a pressing member shown in FIG. 1.

FIG. 5 is a diagram schematically showing an attachment structure of the pressing member 8. As shown, a spherical portion 7a is formed on one end of the pressing bar 7 and received in a bearing 22 formed in the manner of being buried in the pressing member 8. This structure allows the pressing member 8 to swing in the direction indicated by the arrow 500 with the one end of the pressing bar 7 as the center so that orientation of the pressing member 8 can freely be changed.

With this attachment, the pressing member 8 can precisely follow to contact the shape of the external surface of the pelvis of each patient M, regardless of the angle of the pressing bar 7, so that a pressing force can favorably be applied to a target point.

An operation of the thus structured pelvis correction apparatus in this embodiment will be described with reference to FIGS. 1 and 2.

Initially, the pressing bars 7 are pulled apart against the contracting force of the rubber belt 9. While the pressing bars 7 are kept pulled apart as described above, a patient M lies down on the bed 1 with his hip between the pressing bar bearing stands 4. The patient M may lie with his/her face up or down, as desired. For example, a pregnant woman or overweight person who has a large belly preferably lies with her/his face up because the hip of the person does not contact the surface of the bed 10 when the person lies with her/his face down and, therefore, a pressing force is not effectively applied to the pelvis. Then, the vertical positions of the pressing bars 7 are adjusted such that the pressing members 8 of the pressing bars 7 are respectively placed on the target right and left points of the patient M's hip so that a pressing force can be precisely applied to the patient M's pelvis. The pressing bars 7 are then fixed at the adjusted positions using the screws 11.

Thereafter, the pressing bars 7 are released. Thereupon, the pressing bar 7 slides inside the tube member 20 by means of the contracting force of the rubber belt 9 and, consequently, a pressing force is applied to the target right and left points on the patient M's hip by the pressing members 8. The direction in which a pressing force is applied is determined by the inclination angle θ as described above and, by pressing in this direction, a pressing force can be applied to the sacrum around the center of the pelvis from iliac bones in the right and left sides of the pelvis.

Figure 8:
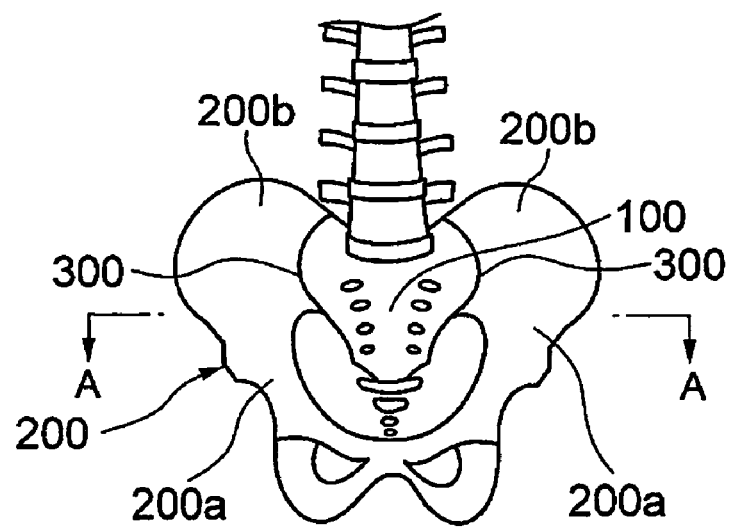
FIG. 8 is a schematic diagram for explaining relationship between a pelvis and a sacrum.
Figure 9:
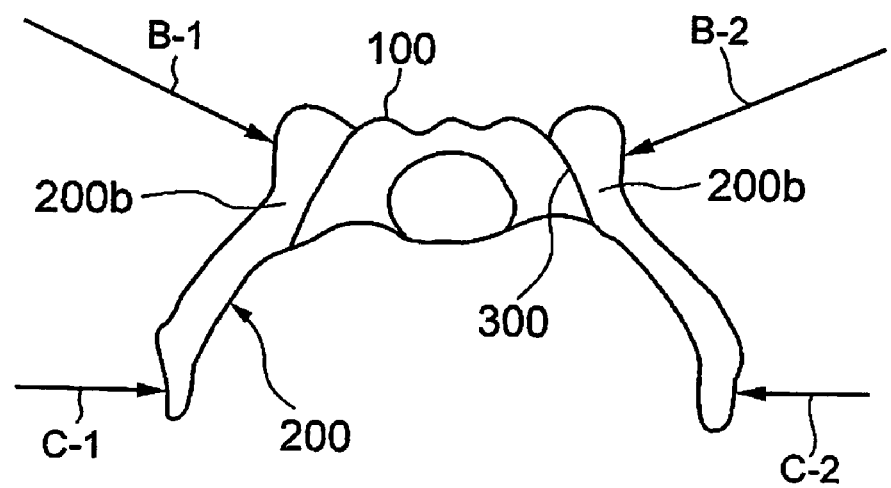
FIG. 9 is a cross sectional view along line A—A in FIG. 8.

FIG. 9 is a schematic cross sectional view along the line A—A in FIG. 8 showing the pelvis and the sacrum. Note that a patient M lies with his/her face down here, so that the upside of the drawing corresponds to the patient M's backside. The iliac bones 200b are pressed at an inclination angle θ from the right and left sides (B-1, B-2) of the patient M, using a pair of pressing bars 7, whereby the auricular surfaces 300 constituting the joint between the pelvis 200 and the sacrum 100 are brought to the proper position. As a result, the laxity of the auricular surfaces 300 between the sacrum 100 and the iliac bones 200b is appropriately eliminated and the pelvis 200 is thus corrected.

Figure 6:
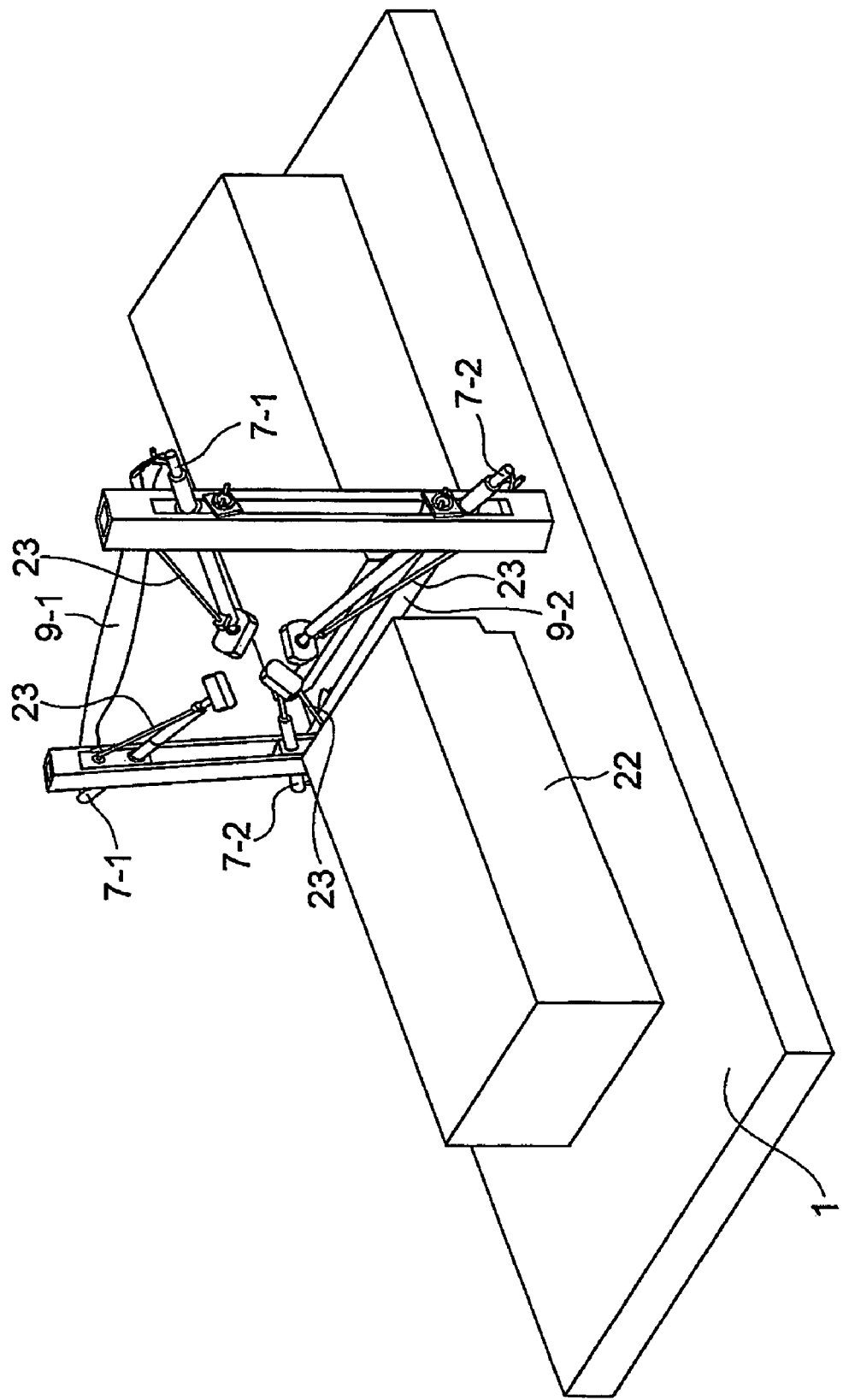
FIG. 6 is a perspective view for showing a pelvis correction apparatus in another embodiment of the present invention.

FIG. 6 shows another preferable embodiment of the present invention, in which identical elements to those in the above-described embodiment are identified by identical reference numerals. This embodiment is characterized in that four pressing bars 7 are provided, two on each side of the bed 1. As shown, each of the pressing bar bearing stands 4 installed in each of the right and left sides of the bed 1 carries two pressing bars 7 including one attached to the upper end of the stand 4 and the other attached to the lower end of the stand 4.

These four pressing bars 7 are constituted of a pair of pressing bars 7-1 attached to the upper ends of the stands 4 and another pair of pressing bars 7-2 attached to the lower ends of the stands 4. The upper pressing bars 7-1 are mounted so as to incline such that the pressing members 8 attached to the respective tip ends of the bars 7-1 are directed downward at a predetermined angle. The lower pressing bars 72 are mounted so as to incline such that the pressing members 8 attached to the respective tip ends of the bars 7-2 are directed upward at a predetermined angle. The inclination angle is determined such that a pressing force is precisely applied to the pelvis of the patient M lying on the bed 1, from four well-balanced directions.

The reference number 23 in the drawing refers to a stretchable member provided to connect the tip end of each pressing bar 7 and the stand 4. The stretchable member in this embodiment is a spring. The spring member 23 supports the associated pressing bar 7 to maintain the bar 7 in an appropriate state when the pressing bar 7 is not used.

It should be noted that rubber belts 9-1 and 9-2 are provided between the upper pair of pressing bars 7-1 and the lower pair of pressing bars 7-2, respectively, as a means for urging the pressing bars 7 to move toward each other.

Figure 10:
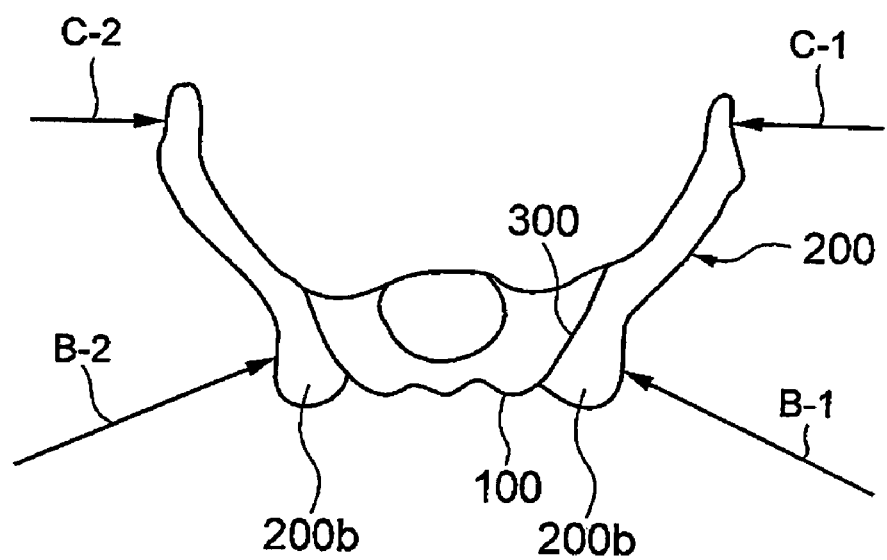
FIG. 10 is a diagram for explaining positional relationship between a patient's pelvis and his/her sacrum when the patient lies with his/her face up.

That is, referring to FIG. 9 which is a cross sectional view of the pelvis 200 and the sacrum 100, the pelvis is pressed not only from directions B-1 and B-2 but also from directions C-1 and C-2. When a patient M lies on the bed 1 with his/her face up, a pressing force is applied to the pelvis from four directions as shown in FIG. 10.

As described above, simultaneous application of a pressing force from above and below the pelvis can produce a preferable effect to bring the auricular surfaces 300 into an appropriate state. That is, laxity of the auricular surfaces 300 or the like can be eliminated in a well-balanced manner.

Pressing from four directions will be more specifically described. Referring to FIG. 9, a pressing force applied in the directions B-1 and B-2 on the side of the iliac bones 200b is larger than a pressing force applied in the directions C1 and C2. This arrangement is effective to keep balanced based on "the principle of lever" and enables well-balanced application of a pressing force to the auricular surface 300. That is, this arrangement enables uniform application of a pressing force to the auricular surface 300.

Differing from the case of FIG. 1, in which only one pair of pressing bars 7 are used, in an embodiment of FIG. 6, the patient M is pressed additionally from below the patient M, using the pressing bars 7. In order to facilitate this setting, a stage 22 is formed in an area along the center of the bed 1 where the patient M lies. This arrangement can facilitate a pressing operation using the lower pair of pressing bars 7-2.

Figure 7:
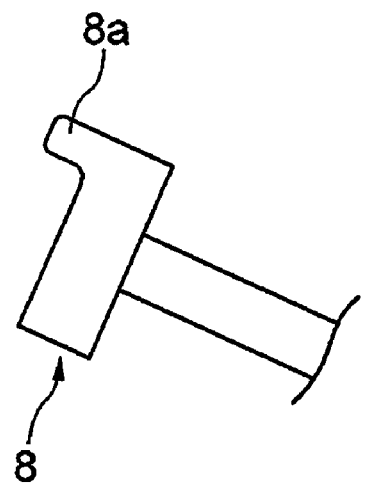
FIG. 7 is a perspective view for showing another example structure of a pressing member provided at one end of a pressing bar.

FIG. 7 shows another exemplary structure of a pressing member 8 attached to one end of the pressing bar 7 of the present invention. That is, a small projection 8a is formed along one edge of the pressing member 8 so that a pressing force can be applied to the tip end of the coxal bone 200a of the sacrum 100 of the patient M lying with his/her face up, as shown in FIG. 10. By pressing such that the small projection 8a is engaged with the edge of the coxal bone 200a, a pressing force can be more precisely transmitted to the target point.

As described above, in this embodiment, as compared with a case in which only a therapist's hand is used to press with, a pressing operation utilizing a more stable path realized by the pressing bar 7 sliding inside the tube member 20 is achieved. Moreover, as a more precise and sufficient force generated by a contracting force of the rubber belt 9 is used, more precise pelvis correction can be attained.

Here, it should be noted that it is necessary to adjust a pressing force depending on a patient M to be treated. For example, a pressing force must be adjusted depending on the muscles or sex of a patient M. This adjustment can be achieved in this embodiment by changing the number of rubber belt 9 installed in the apparatus. Alternatively, a rubber belt 9 having a different cross section may be used.

Similarly, when a spring is used as an urging member instead of a rubber belt, the number of springs in use may be changed or a spring having a different elastic force may be used. Alternatively, a hydraulic cylinder having a decompression valve may be used as an urging member.

Since it is constructed such that the vertical position of the pressing bar 7 is fixed by fixing, using a screw 11, the block 10 and a plate 12 which is placed on the outer surface of the pressing bar baring stand 4 so as to extend across the slit 4c, the height of the pressing bar 7 can be readily adjusted through a simple screwing operation.

As described above, the pelvis correction apparatus according to the present invention enables readily and stable application of a sufficient pressing force at a constant angle to a desired point on the pelvis. Therefore, pelvis correction can be readily and reliably achieved without requiring a trained skill. Consequently, the pelvis correction apparatus according to the present invention is particularly useful in correction of a horizontal opening of the pelvis of a pregnant woman, correction and prevention of reoccurrence of acute hip pain, prevention of hip pain of an overweight person, and so forth.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A pelvis correction apparatus, comprising:
a bed for a patient to receive a treatment;
pressing bars provided so as to move at a constant inclination angle from both sides of the bed toward a pelvis of the patient to receive a treatment while lying on the bed and each of the pressing bars having a pressing member attached to a tip end of the pressing bar to abut on the patient to transmit a pressing force to the pelvis of the patient; and
an urging member which urges the pressing bars to move toward the pelvis of the patient while lying on the bed; and
a structure for mounting the pressing bars has a pressing bar bearing stand which is situated on each of right and left sides of the bed and has a vertically extending horizontal slit formed on the pressing bar bearing stand, and a pressing bar holder which has a tube member allowing the pressing bar to slide inside of the tube member and is fixed such that a vertical position of the pressing bar holder in the slit is adjustable.

2. The pelvis correction apparatus according to claim 1, wherein the pressing bars are provided two on each of the right and left sides of the bed so as to press the pelvis of the patient at two points respectively on right and left sides of the pelvis.

3. The pelvis correction apparatus according to claim 1, wherein the urging member which urges the pressing bar to move toward the pelvis of the patient comprises a stretchable member provided to connect the pressing bars to urge the pressing bars to move toward each other.

4. The pelvis correction apparatus according to claim 1, wherein the urging member which urges the pressing bar to move toward the pelvis of the patient comprises a stretchable member provided to connect the pressing bars to urge the pressing bars to move toward each other.

5. The pelvis correction apparatus according to claim 3, wherein the pressing member attached to the tip end of each pressing bar is provided to be swingable around an axial center of the pressing bar.

6. The pelvis correction apparatus according to claim 2, wherein the pressing member attached to the tip end of each pressing bar is provided to be swingable around an axial center of the pressing bar.

7. The pelvis correction apparatus according to claim 3, wherein the pressing bars are provided two on each of the right and left sides of the bed so as to press the pelvis of the patient at two points respectively on right and left sides of the pelvis.

8. The pelvis correction apparatus according to claim 2, wherein the two pressing bars provided on each side of the bed are mounted such that one pressing bar is mounted at an upper position and the other pressing bar is mounted to a lower position, a first pair of pressing bars mounted at the upper positions are held such that pressing members attached to respective tip ends of the pressing bars incline downward at a predetermined angle and move toward the pelvis while keeping the inclination angle, and a second pair of pressing bars mounted at the lower positions are held such that pressing members attached to respective tip end of the pressing bars incline upward at a predetermined angle and move toward the pelvis while keeping the inclination angle.

9. The pelvis correction apparatus according to claim 1, wherein the pressing member attached to the tip end of each pressing bar is provided to be swingable around an axial center of the pressing bar.

10. The pelvis correction apparatus according to claim 8, wherein the pressing member attached to the tip end of each pressing bar is provided to be swingable around an axial center of the pressing bar.

* * * * *